United States Patent [19]

Bhat et al.

[11] Patent Number: 5,028,417

[45] Date of Patent: Jul. 2, 1991

[54] SUNSCREEN COMPOSITIONS

[75] Inventors: Gulguhji R. Bhat, Ringoes; Martin K. O. Lindemann, Bridgewater; Prakash Naik-Satam, East Windsor, all of N.J.

[73] Assignee: Johnson & Johnson Consumer Products, Inc., New Brunswick, N.J.

[21] Appl. No.: 75,713

[22] Filed: Jul. 20, 1987

[51] Int. Cl.$^5$ .................. A61K 7/40; A61K 7/42; A61K 7/44; A61K 9/12

[52] U.S. Cl. .................. 424/59; 424/47; 424/60; 424/63; 424/64; 514/844; 514/845; 514/847; 514/873; 514/969

[58] Field of Search .................. 424/60, 59

[56] References Cited

U.S. PATENT DOCUMENTS

| | | | |
|---|---|---|---|
| 2,826,169 | 3/1958 | Le Veen | 424/59 |
| 4,514,383 | 4/1985 | Murray et al. | 424/59 |
| 4,663,155 | 5/1987 | Murray et al. | 424/59 |
| 4,663,156 | 5/1987 | Clum et al. | 424/59 |
| 4,759,926 | 7/1988 | Clum et al. | 424/59 |
| 4,761,275 | 8/1988 | Clum et al. | 424/59 |

FOREIGN PATENT DOCUMENTS

| | | | |
|---|---|---|---|
| 962142 | 2/1975 | Canada | 424/60 |
| 2533497 | 7/1975 | Fed. Rep. of Germany | 424/60 |

OTHER PUBLICATIONS

Shirogane et al., Chem. Abs. 1987, vol. 107, Abstract of Japanese Kokai 6284017.

Muto. Chem. Abs. 1987, vol. 106, pp. 23100, 9/13/86, Abstract of Japanese Kokai, 61,207,318, 9/13/86.

Takashima et al., 1987, vol. 106, 23,099k, Abstract of JP 61,194,013, 8/28/86.

Primary Examiner—Dale R. Ore
Attorney, Agent, or Firm—Steven P. Berman

[57] ABSTRACT

Novel sunscreen compositions containing titanium dioxide having a particle size less than 10 m$\mu$ are described as well as methods of protecting the skin from damaging ultraviolet radiation.

6 Claims, No Drawings

SUNSCREEN COMPOSITIONS

BACKGROUND OF THE INVENTION

This invention relates to new and useful ultraviolet radiation sunscreen agents and compositions and to methods of protecting human skin against the potentially harmful effects of sunlight.

Although a tan has long been considered a status symbol indicative of good health and the ability to secure sufficient leisure time to enjoy outdoor activities such as swimming, tennis, golf, skiing and the like, it has become very evident that excessive exposure of the human skin to sunlight is harmful.

It is well documented that human skin is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. This damage potential is also the single most important cause of the premature aging of the skin. In addition, recent studies indicate that chronic sun exposure limits the immuno-response of the human body. There is also evidence that a tan will offer some protection against burning but is quite ineffectual against other types of solar damage.

Growing public awareness that the enjoyment of outdoor activities must go hand in hand with adequate sun protection has led to an unprecedented growth in the area of sunscreen products. A desirable sunscreen product should have the following attributes: protection in both the UV-A and UV-B ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sunscreen ingredients.

The effectiveness of a sunscreen product is indicated by its sun protection factor (SPF). The sun protection factor is the ratio of the amount of exposure (dose) required to produce a minimal erythema reaction in protected skin to the amount required to produce the same reaction in unprotected skin. The dose differs from person to person and is largely dependent on one's genetic predisposition and ethnic origin. If a person would normally require a ten minute exposure to sunlight to develop a minimal erythema reaction, this person when using an SPF 15 sunscreen product should be able to tolerate up to 150 minutes of sunlight without an erythema reaction. Ease of application and cosmetic appeal, on the other hand, rely on subjective evaluations such as visual and tactile impression by the user. Consumer research studies indicate that a sunscreen formulation should rub in easily, leave the skin non-sticky and, above all, should be invisible on the skin after application.

OBJECTS OF THE INVENTION

It is an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing titanium dioxide within a specific particle size range as a sunscreen agent.

DETAILED DESCRIPTION OF THE INVENTION

The sunscreen compositions of the present invention contain as an active sunscreen agent, microfine titanium dioxide of a specific particle size, i.e., less than about 10 m$\mu$. The use of this specific titanium dioxide has been found to enhance solar radiation protection without detracting from desirable cosmetic properties such as ease of application and, most importantly, invisibility.

Titanium dioxide is an inorganic pigment which is widely used in oil and latex paints when a pure white color is desired. It is also employed as an additive in cosmetic products such as bar soaps to enhance the whiteness of the product. This property of titanium dioxide results from its ability to scatter visible radiation. To obtain maximal scattering and hence whiteness, the particle size of commonly used titanium dioxide is generally between 150 and 350 millimicrons (m$\mu$). Titanium dioxide also absorbs and scatters UV-radiation. As is the case with visible light, optimal scattering is a function of the particle size while absorption of UV-radiation is an inherent property of the titanium dioxide molecule itself.

As it is highly desirable that a sunscreen composition after application to the skin should be invisible and scattering of visible light results in an ungainly whitish appearance of the skin, it is essential that the particle size of the selected titanium dioxide maximize UV-B and UV-A absorption and minimize scattering of visible light.

In Japanese Patent Application No. 1981-161,881, there is a disclosure of cosmetics containing 0.1–40% of ultrafinely divided titanium oxide with a particle size of 10–30 m$\mu$ which has been rendered hydrophobic. It is indicated that when hydrophobically treated titanium oxide with a particle size of 10–30 m$\mu$ is blended into cosmetic base materials, it transmits visible light but reflects and scatters the harmful ultraviolet rays. Unfortunately, it has been found that when titanium dioxide of this particle size range is utilized as a sunscreen agent in sunscreen compositions, it results in the loss of one of the most desired properties of such compositions, i.e., invisibility. Products containing titanium dioxide of the particle size disclosed in this application have a white color or cast to them and, therefore, are not invisible. It has been found that when the titanium dioxide of the present invention, i.e., particle size less than about 10 mμ, is utilized, such compositions are invisible and, therefore, highly desirable.

The titanium dioxide useful in the present invention can be prepared by well-known commercial methods. One such method is the classic sulfate process discussed in the Kirk-Othmer Encyclopedia, Vol. 23, on page 143 and set forth in a flow diagram on page 146. The essential step in this process is hydrolysis, under carefully controlled conditions, of an acid solution of titanyl sulfate yielding a hydrous precipitate. This precipitate contains adsorbed sulfuric acid (pH~1) and the resulting pigments are unsuitable for cosmetic applications. To render it suitable for such uses, it is neutralized with barium hydroxide to obtain a pH of about 3 to 6 and calcinated to increase the particle size. As a result of this process, the resulting titanium dioxide is usually present in a mixture with barium sulfate. If desired, for stability purposes, these particles can be coated with stearic acid or other suitable materials.

The sunscreen compositions can contain titanium dioxide as the sole sunscreen agent or in combination with other sunscreen agents such as para-amino benzoic acid and derivatives thereof, oxybenzones, methoxycinnamates, salicylates, vinylogous amides and other known compounds useful as sunscreen agents.

The sunscreen compositions of the present invention contain titanium dioxide as the sole sunscreen agent or in combination with other sunscreen agents and a pharmaceutically extending medium such as a carrier or vehicle which adapts said agents for application to the skin. These compositions can be in either solid, liquid or aerosol form. The sunscreen agents of the present invention can also be incorporated into various cosmetic and personal care products such as hand and body lotions, oils, ointments, lip balm products, facial cosmetics and the like.

The amount of titanium dioxide present in sunscreen compositions or in cosmetic and personal care products may vary greatly but is preferable in a range of about 0.5 to 25% by weight of the total composition. One or more sunscreen agents may be utilized with the combined concentration of said agents, preferably in the range of 5 to 30% by weight of the total composition. Greater amounts of these agents may be incorporated into various products limited only by processing, regulatory and economic considerations.

Specific embodiments of the present invention are illustrated by the following examples. It will be understood, however, that the invention is not confined to the specific limitations set forth in the individual examples, but rather to the scope of the appended claims.

EXAMPLE I

A sunscreen lotion is prepared as follows:

623.5 g deionized water, 1.0 g citric acid, 2.0 g sodium citrate and 1.0 g Carbomer 941 (polymer of acrylic acid crosslinked with an alkyl ether of pentaerythritol) are mixed with an overhead stirrer at room temperature until the Carbomer 941 is completely dissolved. The solution is then homogenized at room temperature for 15 minutes using a Gifford-Wood homo-mixer. The mixture is heated to 80° C. while adding 2.0 g of triethanolamine.

In a separate container, 20.0 g of propylene glycol, 5.0 g of benzyl alcohol, 2.0 g of methyl paraben, 1.0 g of propyl paraben and 10.0 g of glycerine are combined and kept at 50° C. until the parabens are dissolved. It is then added to the other container with stirring at 80° C.

In another container, 100.0 g of lauryl/myristyl benzoate, 100.0 g of isopropyl palmitate, 25.0 g of cetyl alcohol, 5.0 g of dimethicone, 20.0 g of Glucamate SSE-20 (methyl gluceth-20 sesquistearate), 20.0 g of Glucate SS (methyl glucose sesquistearate), 10.0 g of polyoxyethylene (5) soya sterol and 50.0 g of an 80/20 mixture of titanium dioxide and barium sulfate coated with stearic acid are added. The mixture is heated to 80° C. and then homogenized for 10 minutes.

Keeping both phases at 80° C., the latter phase is gradually added to the combined phases while stirring vigorously with an overhead stirrer. The completed mixture is then stirred for an additional 15 minutes before being allowed to gradually cool. When the temperature has reached 45° C., 1.0 g of Dowicil 200 and 1.5 g of fragrance are added. The batch is allowed to cool to room temperature and hand-homogenized.

The finished product has a viscosity of 21000 cps and an SPF of approximately 3 and has the following composition:

| Ingredient | % w/w |
| --- | --- |
| water, deionized | 62.35 |
| citric acid | 0.10 |
| sodium citrate | 0.20 |
| Carbomer 941 | 0.10 |
| triethanolamine | 0.20 |
| propylene glycol | 2.00 |
| benzyl alcohol | 0.50 |
| methyl paraben | 0.20 |
| propyl paraben | 0.10 |
| glycerin | 1.00 |
| lauryl/myristyl benzoate | 10.00 |
| isopropyl palmitate | 10.00 |
| cetyl alcohol | 2.50 |
| dimethicone | 0.50 |
| Glucamate SSE-20 | 2.00 |
| Glucate SS | 2.00 |
| polyoxyethylene (5) soya sterol | 1.00 |
| titanium dioxide | 3.00 |
| barium sulfate | 1.00 |
| stearic acid | 1.00 |
| Dowicil 200 | 0.10 |
| fragrance | 0.15 |

EXAMPLE II

A sunscreen lotion formulation is prepared as follows:

663.5 g of deionized water, 3.0 g of Carbomer 941, 1.0 g of Carbomer 934, 0.5 g ethylenediamine tetraacetate (EDTA), 75.0 g Carboset (acrylic/acrylate copolymer) and 25.0 g of 7.5% w/v ammonium hydroxide solution are combined in a 1.2 liter vessel. The mixture is stirred vigorously at room temperature until complete dissolution is achieved. The solution is then homogenized at room temperature for 15 minutes using a Gifford-Wood homo-mixer. The mixture is then heated to and kept at 70° C.

In a separate container, 10.0 g of stearyl alcohol, 20.0 g glyceryl stearate, 20.0 g of mineral oil, 30.0 g of isostearic acid, 5.0 g of dimethicone, 80.0 g of octyl dimethyl paraamino benzoic acid, 20.0 g of oxybenzone and 40.0 g of octyl methoxycinnamate are heated while stirring to 70° C. After the solution becomes uniform, it is homogenized using a Gifford-Wood homo-mixer. This solution is then added to the first vessel gradually at 70° C. under strong agitation. Stirring is continued and the emulsion is allowed to cool slowly. 3.0 g of benzyl alcohol, 1.0 g of Dowicil 200 and 3.0 g of fragrance are added after the temperature had dropped below 45° C. The batch is allowed to cool to room temperature and hand homogenized. The finished product has a viscosity of about 6500, a SPF of 13.7 and the composition as set forth in Table I hereinafter.

EXAMPLES III-VII

Examples III-VII are prepared according to the general procedure of Example II. These examples are variations of Example II in which increasing percentages of titanium dioxide are added to the oil phase and a corresponding amount of water deleted from the aqueous phase. The compositions and SPF-values are summarized in Table I below:

TABLE I

| Ingredients % w/w | II | III | IV | V | VI | VII |
|---|---|---|---|---|---|---|
| water, deionized | 66.35 | 65.35 | 64.35 | 63.35 | 62.35 | 60.85 |
| Carbopol 941 | 0.30 | 0.30 | 0.30 | 0.30 | 0.30 | 0.30 |
| Carbopol 934 | 0.10 | 0.10 | 0.10 | 0.10 | 0.10 | 0.10 |
| EDTA, di Sodium | 0.05 | 0.05 | 0.05 | 0.05 | 0.05 | 0.05 |
| ammonium hydroxide (7.5%) | 2.50 | 2.50 | 2.50 | 2.50 | 2.50 | 2.50 |
| Carboset | 7.50 | 7.50 | 7.50 | 7.50 | 7.50 | 7.50 |
| stearyl alcohol | 1.00 | 1.00 | 1.00 | 1.00 | 1.00 | 1.00 |
| glyceryl stearate | 2.00 | 2.00 | 2.00 | 2.00 | 2.00 | 2.00 |
| mineral oil | 2.00 | 2.00 | 2.00 | 2.00 | 2.00 | 2.00 |
| isostearic acid | 3.00 | 3.00 | 3.00 | 3.00 | 3.00 | 3.00 |
| dimethicone | 0.50 | 0.50 | 0.50 | 0.50 | 0.50 | 0.50 |
| octyl dimethyl paraaminobenzoic acid | 8.00 | 8.00 | 8.00 | 8.00 | 8.00 | 8.00 |
| oxybenzone | 2.00 | 2.00 | 2.00 | 2.00 | 2.00 | 2.00 |
| octyl methoxycinnamate | 4.00 | 4.00 | 4.00 | 4.00 | 4.00 | 4.00 |
| titanium dioxide | — | 0.60 | 1.20 | 1.80 | 2.40 | 3.30 |
| barium sulfate | — | 0.20 | 0.40 | 0.60 | 0.80 | 1.10 |
| stearic acid | — | 0.20 | 0.40 | 0.60 | 0.80 | 1.10 |
| benzyl alcohol | 0.30 | 0.30 | 0.30 | 0.30 | 0.30 | 0.30 |
| fragrance | 0.30 | 0.30 | 0.30 | 0.30 | 0.30 | 0.30 |
| preservative | 0.10 | 0.10 | 0.10 | 0.10 | 0.10 | 0.10 |
| SPF | 13.7 | 15.5 | 16.6 | 22.8 | —* | 24.9 |

*not measured

The above results clearly demonstrates the excellent SPF enhancing effects of titanium dioxide when used in conjunction with other sunscreen agents.

EXAMPLES VIII-XIII

Examples VIII-XIII are prepared in accordance with the general procedure of Example II. These compositions are the same except for the particle size of the titanium dioxide and have the following formulations:

| Ingredients % w/w | VIII | IX | X | XI | XII | XIII (control) |
|---|---|---|---|---|---|---|
| water, deionized | 59.00 | 59.00 | 59.00 | 59.00 | 59.00 | 64.00 |
| Carbomer 941 | 0.30 | 0.30 | 0.30 | 0.30 | 0.30 | 0.30 |
| ammonium hydroxide | 3.90 | 3.90 | 3.90 | 3.90 | 3.90 | 3.90 |
| sodium EDTA | 0.05 | 0.05 | 0.05 | 0.05 | 0.05 | 0.05 |
| Carboset XL-19 | 7.50 | 7.50 | 7.50 | 7.50 | 7.50 | 7.50 |
| butylated hydroxyanisole | 0.05 | 0.05 | 0.05 | 0.05 | 0.05 | 0.05 |
| vitamin E acetate | 1.00 | 1.00 | 1.00 | 1.00 | 1.00 | 1.00 |
| silicone wax | 1.50 | 1.50 | 1.50 | 1.50 | 1.50 | 1.50 |
| glyceryl monostearate | 2.00 | 2.00 | 2.00 | 2.00 | 2.00 | 2.00 |
| mineral oil | 3.00 | 3.00 | 3.00 | 3.00 | 3.00 | 3.00 |
| isostearic acid | 5.00 | 5.00 | 5.00 | 5.00 | 5.00 | 5.00 |
| dimethicone | 0.50 | 0.50 | 0.50 | 0.50 | 0.50 | 0.50 |

-continued

| Ingredients % w/w | VIII | IX | X | XI | XII | XIII (control) |
|---|---|---|---|---|---|---|
| oxybenzone | 2.00 | 2.00 | 2.00 | 2.00 | 2.00 | 2.00 |
| Parsol MCX (methoxy cinnamate) | 4.00 | 4.00 | 4.00 | 4.00 | 4.00 | 4.00 |
| titanium dioxide | | | | | | |
| 8 millimicrons | 5.00 | 0.00 | 0.00 | 0.00 | 0.00 | 0.00 |
| 10 millimicrons | 0.00 | 5.00 | 0.00 | 0.00 | 0.00 | 0.00 |
| 20 millimicrons | 0.00 | 0.00 | 5.00 | 0.00 | 0.00 | 0.00 |
| 45 millimicrons | 0.00 | 0.00 | 0.00 | 5.00 | 0.00 | 0.00 |
| 70 millimicrons | 0.00 | 0.00 | 0.00 | 0.00 | 5.00 | 0.00 |
| lauryl/myristyl benzoate | 4.50 | 4.50 | 4.50 | 4.50 | 4.50 | 4.50 |
| benzyl alcohol | 0.30 | 0.30 | 0.30 | 0.30 | 0.30 | 0.30 |
| fragrance | 0.30 | 0.30 | 0.30 | 0.30 | 0.30 | 0.30 |
| preservative | 0.10 | 0.10 | 0.10 | 0.10 | 0.10 | 0.10 |
| SPF | 14.7 | 15.9 | 14.2 | 13.5 | 13.4 | 11.6 |
| % Increase over Control | 26.7 | 37.1 | 22.4 | 16.4 | 15.5 | — |

The above formulations of Examples VIII-XIII can be tested for visibility characteristics in accordance with the following procedure: 100 ml/50 cm$^2$ of a formulation to be tested is applied onto the backs of volunteer test subjects, dried for twenty minutes and then the back area is photographed. The photographs are then subjectively rated by fifteen trained individuals using a scale of 0 to 10 corresponding to increasing visibility or whiteness.

When the compositions of Examples VIII-XIII are tested in accordance with the above test procedure, the following results are obtained.

| | VIII | IX | X | XI | XII | XIII |
|---|---|---|---|---|---|---|
| Visibility (average) | 3.8 | 3.7 | 5.9 | 6.7 | 8.6 | 0.9 |

These results show that the incorporation of titanium dioxide enhances the SPF values of the compositions regardless of the particle size of titanium dioxide and further that particle size of the titanium dioxide has an important effect on visibility. The compositions containing titanium dioxide of particle size 8 mµ and 10 mµ are signficiantly less visible than the compositions containing titanium dioxide with larger particle size.

EXAMPLE XIV

A dispersion formulation is prepared as follows: 500 g of an 80/20 mixture of titanium dioxide with barium sulfate coated with stearic acid (62% titanium dioxide) is dispersed in 1500 g of isooctyl stearate by means of a pearl mill (Dyno-Mill Type KDL). The resulting dispersion contains 15.5% titanium dioxide. It has a viscosity of 2600 cps and an SPF of 14.6.

In addition to the preferred embodiments described herein, other embodiments, arrangements and variations within the spirit of the invention and the scope of the appended claims will occur to those skilled in the art.

What is claimed is:

1. A sunscreen composition comprising an extending medium and titanium dioxide having a particle size of less than 10 mµ.

2. The sunscreen composition of claim 1 containing from about 0.5 to 25.0% by weight of the total composition of titanium dioxide.

3. The sunscreen composition of claim 1 containing at least one additional sunscreen agent selected from the group consisting of para-amino benzoic acid and derivatives thereof, oxybenzones, methoxy cinnamates, salicylates and vinylogous amides.

4. The sunscreen composition of claim 1 wherein the sunscreen agent is para-amino benzoic acid and derivatives thereof.

5. A method of protecting human skin from the erythemic effects of ultraviolet radiation which comprises applying to the skin a sunscreen composition containing an extending medium and titanium dioxide having a particle size less than 10 m$\mu$.

6. The method of claim 5 wherein the sunscreen composition contains at least one additional sunscreen agent selected from the group consisting of para-amino benzoic acid and derivatives thereof, oxybenzones, methoxy cinnamates, salicylates and vinylogous amides.

* * * * *